United States Patent
Pryor et al.

(10) Patent No.: US 8,128,279 B2
(45) Date of Patent: Mar. 6, 2012

(54) CLOUD POINT MONITORING SYSTEMS FOR DETERMINING A CLOUD POINT TEMPERATURE OF DIESEL FUEL

(75) Inventors: Bryan K. Pryor, Farmington, MI (US); William C. Albertson, Clinton Township, MI (US)

(73) Assignee: GM Global Technology Operations LLC, Detroit, MI (US)

( * ) Notice: Subject to any disclaimer, the term of this patent is extended or adjusted under 35 U.S.C. 154(b) by 884 days.

(21) Appl. No.: 12/174,056

(22) Filed: Jul. 16, 2008

(65) Prior Publication Data

US 2010/0014553 A1 Jan. 21, 2010

(51) Int. Cl.
*G01N 25/00* (2006.01)

(52) U.S. Cl. ............................................ 374/16; 702/50
(58) Field of Classification Search .............. 374/16–17, 374/20, 28, 43–45, 54; 184/6.4; 73/54.07, 73/54.01, 54.02, 61.45; 702/50; 210/90
See application file for complete search history.

(56) References Cited

U.S. PATENT DOCUMENTS 4,384,472 A * 5/1983 Tournier ...................... 73/30.01
(Continued)

*Primary Examiner* — Lisa Caputo
*Assistant Examiner* — Tania Courson
(74) *Attorney, Agent, or Firm* — Cantor Colburn LLP

(57) ABSTRACT

Cloud point monitoring systems for determining a cloud point of diesel fuel are provided. In one exemplary embodiment, a cloud point monitoring system determines a cloud point temperature value utilizing signals indicating a viscosity level of diesel fuel and a temperature of the diesel fuel.

15 Claims, 9 Drawing Sheets

U.S. PATENT DOCUMENTS

| | | | |
|---|---|---|---|
| 4,478,197 A * | 10/1984 | Yasuhara et al. | 123/514 |
| 5,311,447 A * | 5/1994 | Bonne | 702/50 |
| 5,458,767 A * | 10/1995 | Stone | 210/90 |
| 5,486,107 A * | 1/1996 | Bonne | 431/121 |
| 5,887,572 A * | 3/1999 | Channing | 123/514 |
| 6,721,649 B2 * | 4/2004 | Knott et al. | 701/114 |
| 6,827,484 B2 * | 12/2004 | Tsang et al. | 374/20 |
| 6,966,692 B2 | 11/2005 | Tsang et al. | |
| 7,676,316 B2 * | 3/2010 | Lunati et al. | 701/103 |
| 7,841,769 B2 * | 11/2010 | Ma et al. | 374/147 |
| 2008/0093172 A1 | 4/2008 | Albertson et al. | |
| 2008/0223114 A1 | 9/2008 | Albertson et al. | |
| 2009/0044444 A1 * | 2/2009 | Sugano | 44/300 |
| 2009/0141769 A1 * | 6/2009 | Baldwin et al. | 374/144 |
| 2010/0033372 A1 * | 2/2010 | Pryor et al. | 342/357.09 |
| 2010/0175370 A1 * | 7/2010 | Bunge | 60/277 |

\* cited by examiner

CLOUD POINT MONITORING SYSTEMS FOR DETERMINING A CLOUD POINT TEMPERATURE OF DIESEL FUEL

FIELD OF THE INVENTION

Exemplary embodiments of the present invention relate generally to diesel fuel systems, and more particularly to diesel fuel cloud point monitoring systems.

BACKGROUND

At relatively cold ambient temperatures diesel fuel can partially solidify (gel) due to the formation of waxy crystals. Gelling of the fuel can affect engine performance, including causing the engine to cease operation. Formation of the waxy crystals causes the fuel to become cloudy. The cloud point temperature of the fuel is the temperature at which the wax crystals begin to form. The cloud point temperature of diesel fuel can vary widely even within fuel of the same grade (i.e., No. 2 diesel), and also varies widely when biodiesel fuels are mixed with diesel fuel. Diesel fuels are generally blended so as to have a cloud point temperature which is appropriate for the location in which the fuel is sold. Therefore, it may be desirable to detect and monitor the cloud point temperature of the diesel fuel, since vehicles may take on fuel in a relatively warmer region where gelling is not a concern and due to their long travel range carry the fuel blended for the warmer region to relatively colder regions where gelling is possible. A problem associated with some existing cloud point monitoring devices is that wax crystals can form in such a way that they may not be detected in the diesel fuel, resulting in an inaccurate determination of the cloud point temperature, thereby limiting the ability to take appropriate measures to prevent gelling of the diesel fuel.

Accordingly, it is desirable to develop cloud point monitoring systems having improved accuracy with regard to detection and monitoring of the cloud point temperature.

SUMMARY OF THE INVENTION

A cloud point monitoring system in accordance with an exemplary embodiment is provided. The cloud point monitoring system includes a pumping device configured to pump diesel fuel therefrom in response to a voltage being applied to the pumping device. The cloud point monitoring system further includes a temperature sensor configured to generate a temperature signal indicating a temperature of diesel fuel in the pumping device. The cloud point monitoring system further includes a viscosity sensor configured to generate a viscosity signal having a characteristic indicative of a viscosity level of the diesel fuel in the pumping device. The cloud point monitoring system further includes a controller configured to generate the voltage to induce the pumping device to pump diesel fuel therefrom. The controller is further configured to determine a temperature value based on the temperature signal. The controller is further configured to determine a cloud point temperature value associated with the diesel fuel based on the temperature value and the characteristic of the viscosity signal.

A motor vehicle in accordance with another exemplary embodiment is provided. The motor vehicle includes a diesel engine configured to receive diesel fuel from a fuel tank. The motor vehicle further includes a cloud point monitoring system receiving a portion of the diesel fuel from the fuel tank. The cloud point monitoring system includes a pumping device configured to receive the portion of the diesel fuel and to pump diesel fuel therefrom in response to a voltage being applied to the pumping device. The cloud point monitoring system further includes a temperature sensor configured to generate a temperature signal indicating a temperature of diesel fuel in the pumping device. The cloud point monitoring system further includes a viscosity sensor configured to generate a viscosity signal having a characteristic indicative of a viscosity level of the diesel fuel in the pumping device. The cloud point monitoring system further includes a controller configured to generate the voltage to induce the pumping device to pump the diesel fuel therefrom. The controller is further configured to determine a temperature value based on the temperature signal. The controller is further configured to determine a cloud point temperature value associated with the diesel fuel based on the temperature value and the characteristic of the viscosity signal.

BRIEF DESCRIPTION OF THE DRAWINGS

Other features, advantages and details appear, by way of example only, in the following description of embodiments, the description referring to the drawings in which.

DESCRIPTION OF THE EMBODIMENTS

Figure 1:
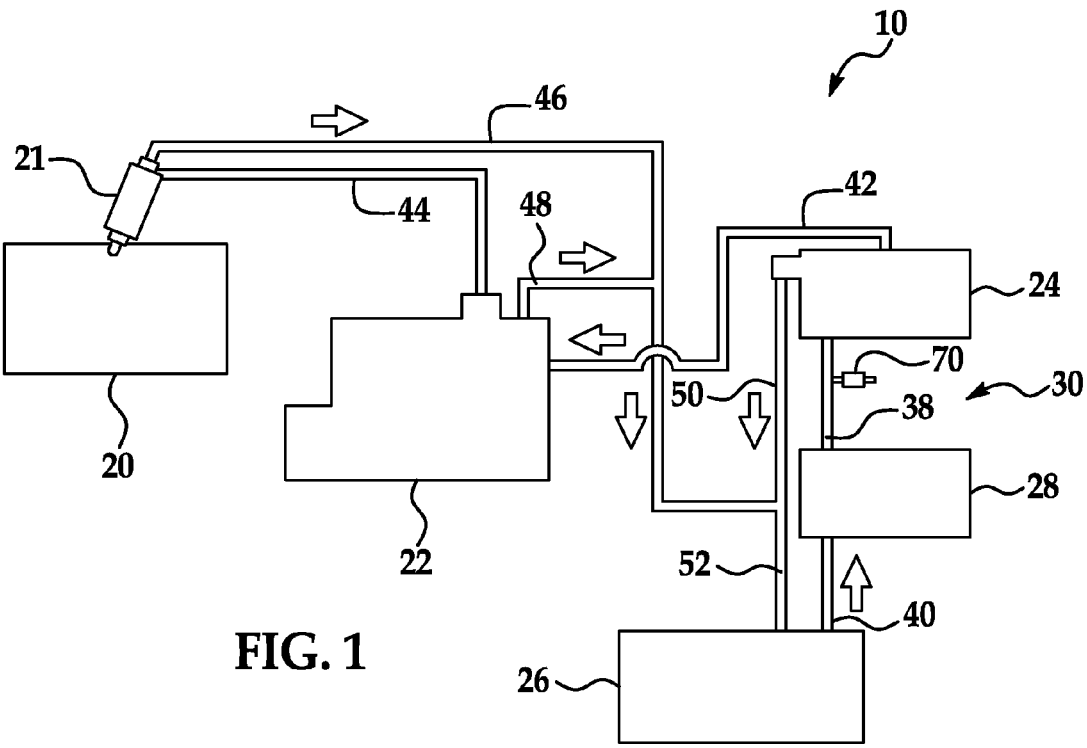
FIG. 1 is a schematic of a motor vehicle having a cloud point monitoring system in accordance with an exemplary embodiment.

Referring to FIG. 1, a motor vehicle 10 having a cloud point monitoring system 30 in accordance with an exemplary embodiment is provided. The motor vehicle 10 further includes an engine 20, a fuel injector 21, a fuel pump 22, a fuel filter 24, a fuel tank 26, a feed pump 28, tubular conduits 40, 42, 44, 46, 48, 50, 52 which fluidly interconnect various of the aforementioned components for communication of diesel fuel between them, and a diesel fuel conduit 38. Associated with diesel fuel conduit 38 is a cloud point monitoring system 30 which is provided to determine and monitor a cloud point temperature for diesel fuel based on a viscosity of the diesel fuel utilized by the vehicle 10. While cloud point monitoring system 30 is associated with diesel fuel conduit 38 in the exemplary embodiments shown, association with other tubular conduits of a fuel system is also believed to be possible and within the scope of the present invention. Further, while illustrated in the various exemplary embodiments described herein in conjunction with engine 20 for vehicle 10, cloud point monitoring system 30 may be employed in fuel systems for all manner of diesel engines.

The fuel injector 21, fuel pump 22, fuel filter 24, fuel tank 26, fuel pump 28, tubular conduits 40, 42, 44, 46, 48, 50 and 52, diesel fuel conduit 38 and monitoring system 30 are elements of a fuel system for delivering diesel fuel to diesel engine 20. The feed pump 28 fluidly communicates with the tubular conduit 40 and the diesel fuel conduit 38. The feed pump 28 is configured to pump diesel fuel from the fuel tank 26 through the tubular conduit 40 and the diesel fuel conduit 38 to the fuel filter 24.

The fuel filter 24 fluidly communicates with the diesel fuel conduit 38 and the tubular conduits 42, 50. The fuel filter 24 is configured to filter the diesel fuel flowing therethrough and to allow a portion of the diesel fuel to flow through the tubular conduit 42 to the fuel pump 22. The fuel filter 24 is further configured to return a portion of the received diesel fuel through the tubular conduits 50, 52, to the fuel tank 26.

The fuel pump 22 fluidly communicates with the tubular conduits 42, 44 and 48. The fuel pump 22 is configured to pump diesel fuel through the tubular conduit 44 to the fuel injector 21. The pressure of the diesel fuel within the tubular conduit 44 is at a relatively high pressure level. The diesel pump 22 is further configured to return some residual diesel fuel through the tubular conduits 48, 52 to the fuel tank 26.

The fuel injector 21 is operably coupled to the engine 20 and fluidly communicates with the tubular conduits 44, 46. The fuel injector 21 is configured to receive diesel fuel from the fuel pump 22 via the tubular conduit 44 at a relatively high pressure level. The fuel injector 21 is further configured to inject a first portion of the received diesel fuel into the engine 20. A second portion of diesel fuel received by the fuel injector 21 is routed through the tubular conduits 46, 52 back to the fuel tank 26.

Figure 2:
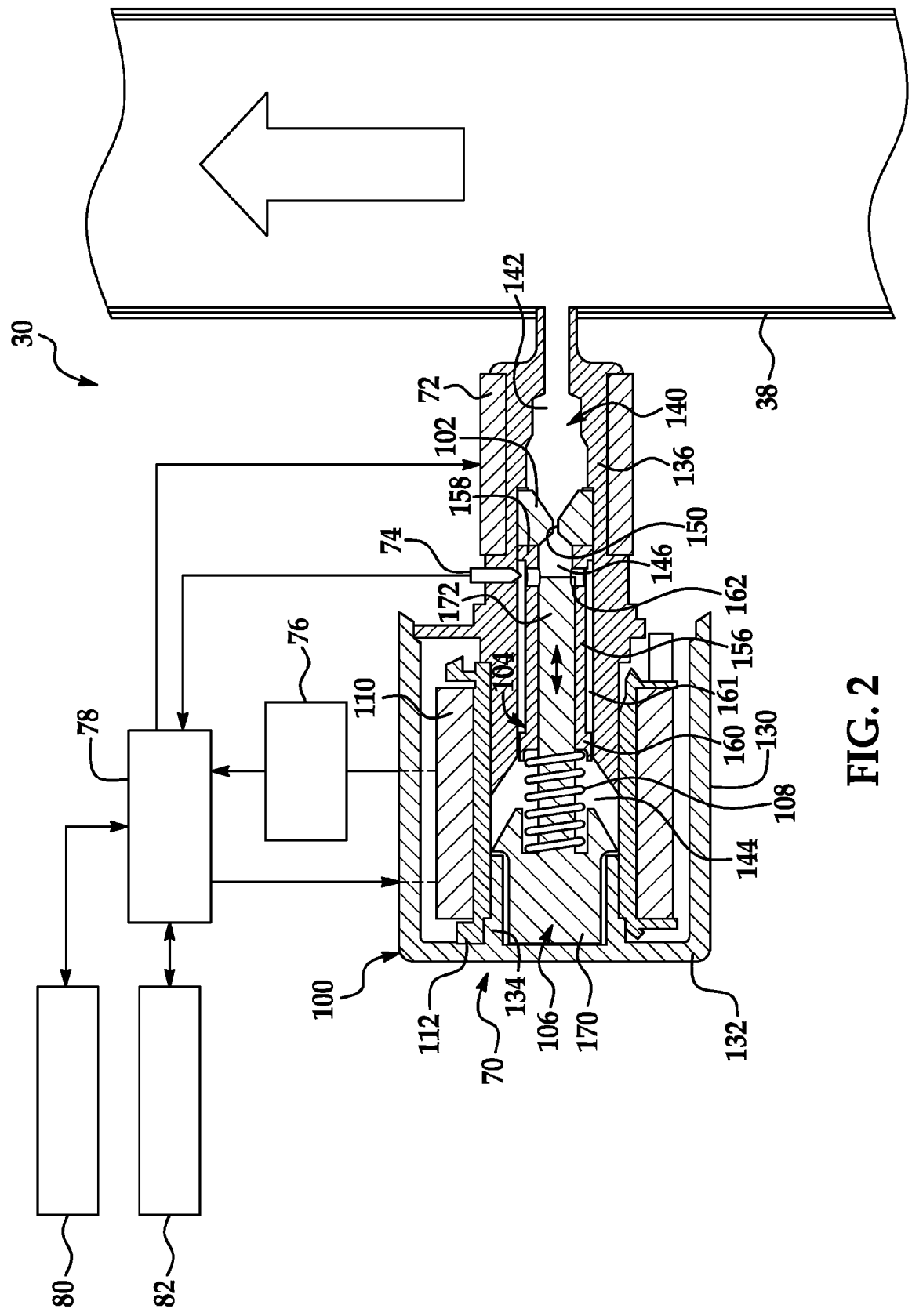
FIG. 2 is a schematic of the cloud point monitoring system utilized in the motor vehicle of FIG. 1 in accordance with another exemplary embodiment.

Referring to FIG. 2, the cloud point monitoring system 30 that determines a cloud point temperature of diesel fuel will now be explained in greater detail. The cloud point monitoring system 30 includes a pumping device 70, a thermal device 72, a temperature sensor 74, a current sensor 76, a controller 78, a memory device 80, and a display device 82. The cloud point monitoring system 30 is fluidly coupled to the diesel fuel conduit 38 and receives a portion of the diesel fuel flowing through the diesel fuel conduit 38, to determine the cloud point temperature of the diesel fuel.

The pumping device 70 is provided to pump diesel fuel from the diesel fuel conduit 38 into the pumping device 70 and to pump the diesel fuel from the pumping device 70 into the diesel fuel conduit 38, in response to a control signals from the controller 78. The pumping device 70 includes a housing 100, a restriction member 102, a sleeve member 104, an armature 106, a spring 108, an electrical coil 110, and a bobbin 112.

The housing 100 is provided to enclose the remaining portions of the pumping device 70. The housing 100 includes an outer wall 130, an end wall 132, an inner wall 134, and an inlet-outlet portion 136. The outer wall 130 is tubular-shaped and is enclosed at a first end by the end wall 132. The inner wall 134 is substantially tubular-shaped and extends from the end wall 132 in a similar direction as the outer wall 130. The inner wall 134 is centered within interior region defined by the outer wall 130 and a diameter of the inner wall 134 is less than the diameter of the outer wall 130. The inlet-outlet portion 136 is coupled at a second end of the outer wall 130. The inlet-outlet portion 136 is further coupled to the diesel fuel conduit 38 and fluidly communicates with the diesel fuel conduit 38. The outer wall 130, the end wall 132 and the inlet-outlet portion 136 define an interior space 140. Housing 100 may be made from any suitable material to house the other components of pumping device 70. In an exemplary embodiment, housing 100 comprises a portion of the magnetic flux path for pumping device 70 and may be formed from a magnetic material, including numerous ferrous alloys.

The restriction member 102 is disposed in the inlet-outlet portion 136 in the interior space 140. The restriction member 102 has an aperture 150 extending therethrough. The restriction member 102 partitions the interior space 140 into a region 142 and a region 144, including the space within chamber 146. The region 142 is disposed proximate to the diesel fuel conduit 38.

The sleeve member 104 is disposed in the region 144 proximate to the restriction member 102. The sleeve member 104 includes a tubular portion 156 and finger portions 158, 160. The finger portion 158 is disposed at a first end of the tubular portion 156 and contacts both the inlet-outlet portion 136 and the restriction member 102. The finger portion 160 is disposed at a second end of the tubular portion 156 within the inlet-outlet portion 136. Finger portion 160 is disposed within inlet-outlet portion so as to permit fuel to flow between region 142 and region 144, including into and out of chamber 346. The tubular portion 156 includes an aperture 162 extending therethrough for allowing diesel fuel to flow therethrough into a gap or annulus 161 between the tubular portion 156 and the inlet-outlet portion 136. Restriction member 102 and sleeve member 104 may be made from any suitable material which is operative to receive and contain diesel fuel, including a number of metals and engineering plastics that are compatible with the organic solvent and other constituents of diesel fuels, including biodiesel fuels. In one exemplary embodiment, restriction member 102 and sleeve member 104 may comprise a single component.

The armature 106 is provided to pump diesel fuel into the pumping device 70 when the armature 106 moves in the first direction (leftwardly to the position shown in FIG. 2) and to pump diesel fuel from the pumping device 70 when the armature 106 moves in a second direction (rightwardly from the position shown in FIG. 2) opposite the first direction. The armature 106 includes a body portion 170 coupled to a piston portion 172 and may be constructed from steel or other suitable materials. The armature is disposed in the region 144 and the piston 172 is disposed within the tubular portion 156 of the sleeve member 104. The piston 172 is configured to slide within the sleeve member 106. The spring 108 is disposed around a portion of the piston portion 172, and a first end of the spring 108 abuts against the body portion 170 and a second end of the spring of 108 abuts against the sleeve member 104. The spring 108 biases the armature 106 in the first direction (leftwardly to the position shown in FIG. 2). During operation, when the controller 78 applies a voltage on the electrical coil 110, the armature 106 moves in the second direction (rightwardly from the position shown in FIG. 2). Thereafter, when the controller 78 does not apply a voltage on the electrical coil 110, the spring 108 biases the armature 106 in the first direction (leftwardly to the position shown in FIG.

2). The armature 106 may be made from any suitable magnetic material, including ferromagnetic materials, such as various ferrous materials. In one exemplary embodiment, armature 106 comprises iron or an iron alloy.

The piston 172, the sleeve member 104, and the restriction member 102 define a chamber 146. Diesel fuel is either pumped into the chamber 146 from the diesel fuel conduit 38 or pumped out of the chamber 146 into the diesel fuel conduit 38.

The bobbin 112 is provided to support the electrical coil 110 thereon. The bobbin 112 is substantially tubular-shaped and is disposed around the inner wall 134 and on a portion of the inlet-outlet portion 136. The bobbin 112 is constructed of a non-magnetic material, such as an engineering plastic or non-magnetic metal.

The electrical coil 110 comprising a plurality of windings of a suitable conductive material is provided to receive a voltage from the controller 78 and to urge the armature 106 in a first direction toward the restriction member 102 to pump diesel fuel from the pumping device 70 into the diesel fuel line 38. The electrical coil 110 is further provided to allow the spring 108 to urge the armature 106 in a second direction toward the end wall 132 to draw or pump diesel fuel from the diesel fuel line 38 into the pumping device 70, when the voltage is removed from the electrical coil 110. In one exemplary embodiment, coil 110 may be wound from any suitable conductive material including various copper, aluminum and nickel alloys and the like. The electrical coil 110 is disposed around the bobbin 112 in the region 144 of the interior space 140.

Figure 3:
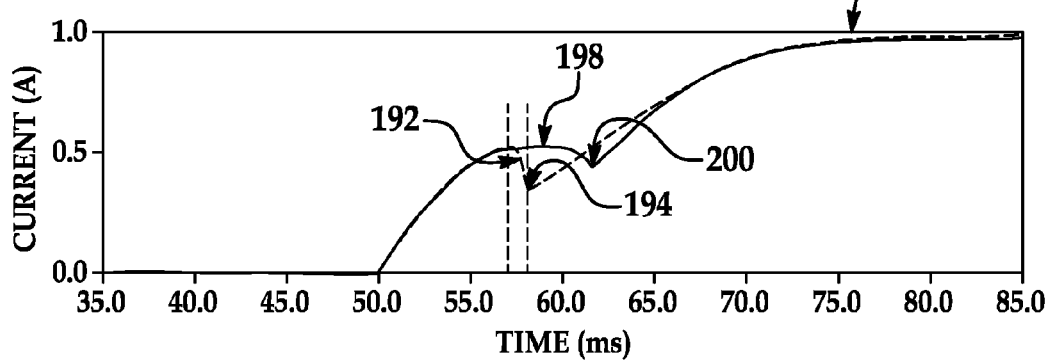
FIG. 3 is a graph having curves indicating electrical currents generated in a pumping device in the cloud point monitoring system of FIG. 2.

Referring to FIG. 3, a graph 190 of current in the coil as a function of time in the form of electrical current curves 192, 198 is illustrated. The electrical current curve 192 represents an electrical current generated in the electrical coil 110 during movement of the armature 106 in a second direction (rightwardly from the position shown in FIG. 2) when diesel fuel within the pumping device 70 is not at a cloud point temperature and does not have wax crystals therein. The electrical current curve 192 has an inflection point 194 that is obtained when the piston 172 of the armature 106 has moved rightwardly and is disposed against the restriction portion 102. The electrical current curve 198 represents an electrical current generated in the electrical coil 110 during movement of the armature 106 in a second direction (rightwardly from the position shown in FIG. 2) when diesel fuel within the pumping device 70 is at a cloud point temperature and has wax crystals therein. The electrical current curve 198 also has an inflection point 200 that is obtained when the piston 172 of the armature 106 has moved rightwardly and is disposed against the restriction member 102.

Figure 4:
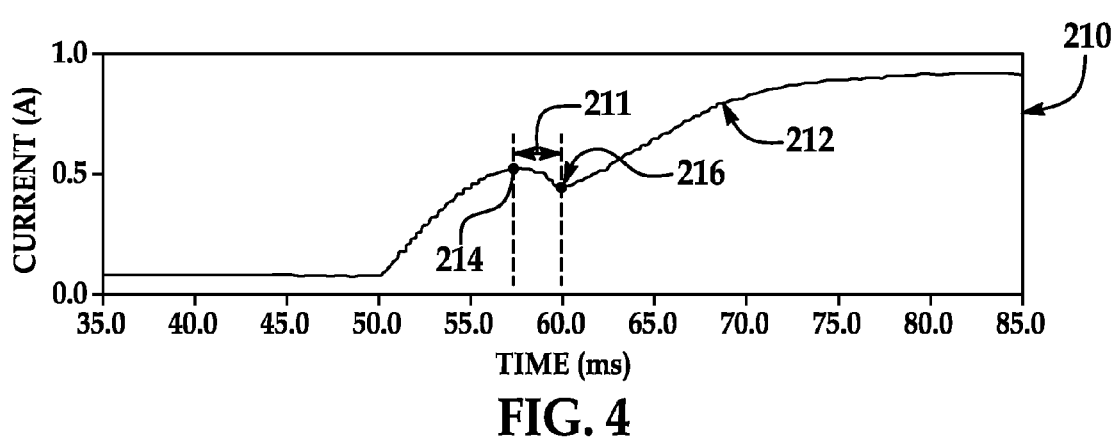
FIG. 4 is a graph having a curve indicating an electrical current generated in a pumping device in the cloud point monitoring system of FIG. 2.

Before proceeding with a detailed explanation of determining a cloud point temperature utilizing the pumping device 70, a general overview will be provided. In particular, when diesel fuel is at or below a cloud point temperature, wax crystals can form in the diesel fuel. The cloud point temperature may vary during use of the fuel system and engine 20 upon refueling, the addition of various fuel additives and other factors. Referring to FIG. 4, a graph of electric current in the coil as a function of time in the form of an electrical current curve 212 is illustrated. The electrical current curve 212 represents an electrical current generated in the electrical coil 110 during movement of the armature 106 in a second direction (rightwardly from the position shown in FIG. 2) when diesel fuel within the pumping device 70 is at the cloud point temperature and the diesel fuel has a relatively high viscosity level because of wax crystals therein. When a time interval 211 of a portion of the curve 212 having a negative slope (e.g., portion of the curve 212 from inflection point 214 to inflection point 216) is greater than or equal to a predetermined time interval, the controller 78 determines that the diesel fuel has a relatively high viscosity level due to wax crystals in the diesel fuel. In other words, when the diesel fuel has wax crystals therein resulting in a relatively high viscosity level, the armature 106 moves relatively slowly in a second direction (rightwardly from the position shown in FIG. 2), and has a travel time greater than or equal to a predetermined time interval. Further, when wax crystals are detected as the diesel fuel is cooled in the manner described, the controller 78 can then determine the cloud point temperature based on the signal from the temperature sensor 74. It should be noted that the time interval 211 of a portion of the curve 212 having a negative slope (e.g., portion of the curve 212 from point 214 to point 216) is a characteristic that is indicative of the viscosity level of the diesel fuel, with increasing time intervals associated with increasing viscosity levels as the fuel is cooled. Thus, the current sensor may be termed a viscosity sensor and the current signal obtained therefrom may be termed a viscosity signal.

Referring again to FIG. 2, the thermal device 72 is disposed adjacent to the inlet-outlet portion 136. The thermal device 72 is configured to cool the inlet-outlet portion 136 and the diesel fuel therein and particularly the fuel in chamber 146, in response to receiving a cooling control signal from the controller 78. In one exemplary embodiment, the thermal device 72 is a Peltier cell; however, other suitable means for cooling may also be employed within the scope of the present invention.

The temperature sensor 74 is disposed on the inlet-outlet portion 136 and fluidly communicates with the diesel fuel within the inlet-outlet portion 136. The temperature sensor 74 is configured to generate a temperature signal indicative of a temperature of the diesel fuel in the inlet-outlet portion 136, and particularly the fuel within chamber 146 which is received by the controller 78. In one exemplary embodiment, the temperature sensor 74 comprises a thermocouple.

The current sensor 76 is provided to generate a signal indicative of an amplitude of an electrical current in the electrical coil 110 and also of viscosity as described herein, which is received by the controller 78. The current sensor 76 is electrically coupled to the electrical coil 110 and to the controller 78.

The controller 78 is electrically coupled to the thermal device 72, the temperature sensor 74, the current sensor 76, the memory device 80, the display device 82, and the electrical coil 110. The controller 78 is provided to determine a cloud point temperature of the diesel fuel based on signals received from the temperature sensor 74 and the current sensor 76, as will be explained in greater detail below. In one exemplary embodiment, the controller 78 comprises a microprocessor. The memory device 80 is provided to store data and values generated by the controller 78 therein. The display device 82 is provided to display data and values, including cloud point temperature values, generated by the controller 78.

Figure 5:
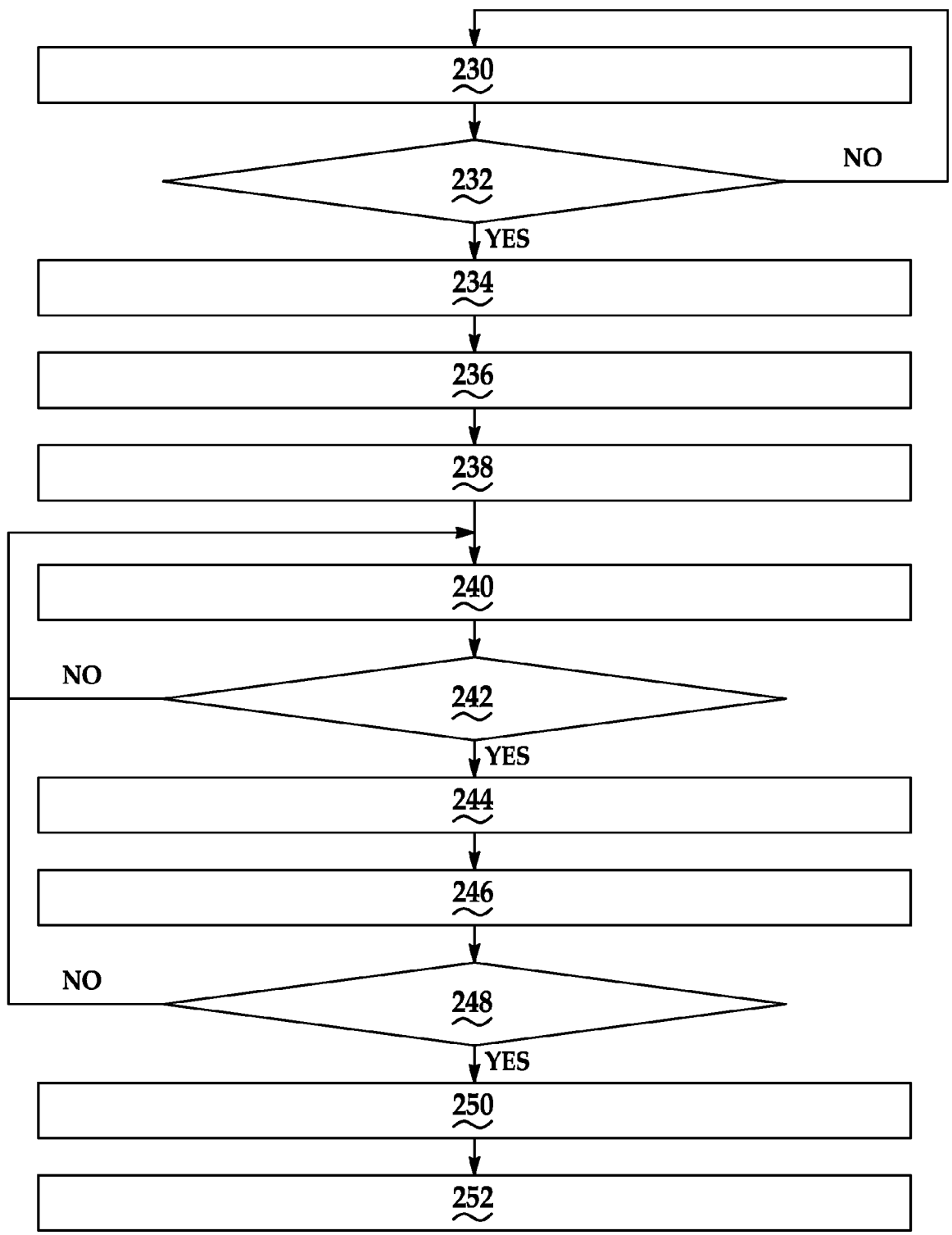
FIG. 5 is a flowchart of a method for determining a cloud point temperature value for diesel fuel utilizing the cloud point monitoring system of FIG. 2, in accordance with another exemplary embodiment.

Referring to FIG. 5, a flowchart of a method for determining a cloud point temperature value indicating a cloud point temperature of diesel fuel, utilizing the cloud point monitoring system 30, will now be explained with reference to steps 230-252. At step 230, the controller 78 receives a first temperature signal from the temperature sensor 74 indicative of a temperature of diesel fuel in the pumping device 70, and determines a first temperature value based on the temperature signal. At step 232, the controller 78 makes a determination as to whether the first temperature value is within a first predetermined temperature range. If the value of step 232 equals "yes", the method advances to step 234. Otherwise, the method returns to step 230. At step 234, the controller 78 iteratively generates a first voltage to cycle the pumping device 70 to pump fresh diesel fuel into the pumping device 70. At step 236, the controller 78 receives a second temperature signal from the temperature sensor 74 indicative of a temperature of diesel fuel in the pumping device 70, and determines a second temperature value based on this signal. At step 238, the controller 78 generates a cooling control signal to induce the thermal device 72 to cool diesel fuel in the pumping device 70. At step 240, the controller 78 receives a third temperature signal from the temperature sensor 74 indicative of a temperature of diesel fuel in the pumping device 70, and determines a third temperature value based on this signal. At step 242, the controller 78 makes a determination as to whether the third temperature value is less than or equal to a previous temperature value minus 2° C., or other decrement value suitable to indicate the temperature is changing. If the value of step 242 equals "yes", the method advances to step 244. Otherwise, the method returns to step 240. At step 244, the controller 78 generates a second voltage to induce the pumping device 70 to pump diesel fuel from the pumping device 70. At step 246, the controller 78 receives a current signal from the current sensor 76 electrically coupled to the pumping device 70, during generation of the second voltage. At step 248, the controller 78 makes a determination as to whether the diesel fuel is at a cloud point temperature, based on the current signal. In particular, the controller 78 determines a travel time of the armature 106 based upon the current signal, and if the travel time is greater than a predetermined time interval, the controller 78 determines that the diesel fuel is at the cloud point temperature. In one exemplary embodiment the predetermined time interval relates to a time interval representative of diesel fuels that are above the cloud point temperature. If the value of step 248 equals "yes", the method advances to step 250. Otherwise, the method returns to step 240. At step 250, the controller 78 sets a cloud point temperature value equal to the third temperature value and (i) displays the cloud point temperature value on the display device 82, and (ii) stores the cloud point temperature value in the memory device 80. At step 252, the controller 78 stops generating the cooling control signal to induce the thermal device 72 to stop cooling the diesel fuel in the pumping device 70. The method and steps 230-252 may be repeated continuously in conjunction with the operation of vehicle 10 or engine 20.

Figure 6:
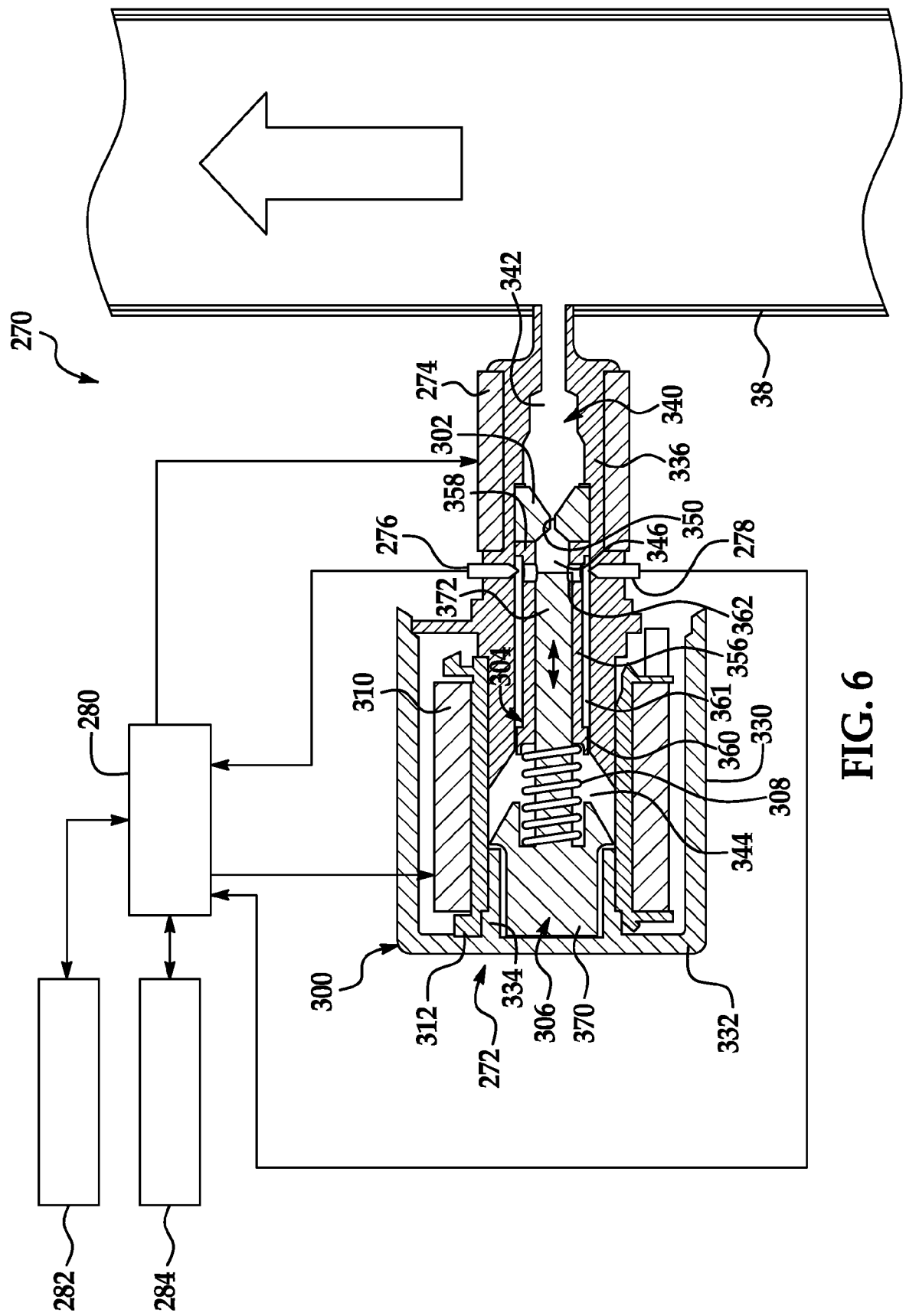
FIG. 6 is a schematic of another cloud point monitoring system that can be utilized in the motor vehicle of FIG. 1, in accordance with a second exemplary embodiment.

Referring to FIG. 6, a second exemplary embodiment of a cloud point monitoring system 270 that can be utilized in the vehicle 10, instead of the cloud point monitoring system 30, will now be explained. The cloud point monitoring system 270 includes a pumping device 272, a thermal device 274, a temperature sensor 276, a pressure sensor 278, a controller 280, a memory device 282, and a display device 284. The cloud point monitoring system 270 is fluidly coupled to the diesel fuel conduit 38 and receives a portion of the diesel fuel flowing through the diesel fuel conduit 38, to determine the cloud point temperature of the diesel fuel.

The pumping device 272 is provided to draw or pump diesel fuel from the diesel fuel conduit 38 into the pumping device 272 and to pump the diesel fuel from the pumping device 272 into the diesel fuel conduit 38, in response to a control signals from the controller 280. The pumping device 272 includes a housing 300, a restriction member 302, a sleeve member 304, an armature 306, a spring 308, an electrical coil 310 and a bobbin 312.

The housing 300 is provided to enclose the remaining portions of the pumping device 272. The housing 300 includes an outer wall 330, an end wall 332, an inner wall 334, and an inlet-outlet portion 336. The outer wall 330 is enclosed at a first end by the end wall 332. The inner wall 334 is tubular-shaped and extends from the end wall 332 in a similar direction as the outer wall 330. The inner wall 334 is centered within an interior region defined by the outer wall 330, and the diameter of the inner wall 334 is less than the diameter of the outer wall 330. The inlet-outlet portion 336 is coupled at a second end of the outer wall 330. The inlet-outlet portion 336 is further coupled to the diesel fuel conduit 38 and fluidly communicates with the diesel fuel conduit 38. The outer wall 330, the end wall 332 and the inlet-outlet portion 336 define an interior space 340.

The restriction member 302 is disposed in the inlet-outlet portion 336 in the interior space 340. The restriction member 302 has an aperture 350 extending therethrough. The restriction member 302 partitions the interior space 340 into a region 342 and a region 344, including the space within chamber 346. The region 342 is disposed proximate to the diesel fuel conduit 38.

The sleeve member 304 is disposed in the region 344 proximate to the restriction member 302. The sleeve member 304 includes a tubular portion 356 and finger portions 358, 360. The finger portion 358 is disposed at a first end of the tubular portion 356 and contacts both the inlet-outlet portion 336 and the restriction member 302. The finger portion 360 is disposed at a second end of the tubular portion 356 within the inlet-outlet portion 336. Finger portion is disposed within inlet-outlet portion so as to permit fuel to flow between region 342 and region 344, including into and out of chamber 346. The tubular portion 356 includes an aperture 362 extending therethrough for allowing diesel fuel to flow therethrough into a gap or annulus 361 between the tubular portion 356 and the inlet-outlet portion 336.

The armature 306 is provided to draw or pump diesel fuel into the pumping device 272 when the armature 306 moves in the first direction (leftwardly to the position shown in FIG. 6) and to pump diesel fuel from the pumping device 272 when the armature 306 moves in a second direction (rightwardly from the position shown in FIG. 6) opposite the first direction. The armature 306 includes a body portion 370 coupled to a piston 372 and may be constructed from steel or other suitable material. The armature 306 is disposed in the region 344 and the piston 372 is disposed within the tubular portion 356 of the sleeve member 304. The piston 372 is configured to slide within the sleeve member 304. The spring 308 is disposed around a portion of the piston 372 and a first end of the spring 308 abuts against the body portion 370 and a second end of the spring of 308 abuts against the sleeve member 304. The spring 308 biases the armature 306 in the first direction (leftwardly to the position shown in FIG. 6). During operation, when the controller 280 applies a voltage on the electrical coil 310, the armature 306 moves in the second direction (rightwardly from the position shown in FIG. 6). Thereafter, when the controller 280 does not apply a voltage on the electrical coil 310, the spring 308 biases the armature 306 in the first direction (leftwardly to the position shown in FIG. 6). The armature 306 may be made from any suitable magnetic material, including ferromagnetic materials, such as various ferrous materials. In one exemplary embodiment, armature 306 comprises iron or an iron alloy.

The piston 372, the sleeve member 304, and the restriction member 302 define a chamber 346. Diesel fuel is either drawn into the chamber 346 from the diesel fuel conduit 38 or pumped out of the chamber 346 into the diesel fuel conduit 38.

The bobbin 312 is provided to support the electrical coil 310 thereon. The bobbin 312 is disposed around the inner wall 334 and on a portion of the inlet-outlet portion 336. The bobbin 312 is constructed of a non-magnetic material.

The electrical coil 310 is provided to receive a voltage from the controller 280 and to urge the armature 306 in a first direction toward the restriction member 302 to pump diesel fuel from the pumping device 272 into the diesel fuel line 38. The electrical coil 310 is further provided to be disengaged and allow the spring 308 to urge the armature 306 in a second direction toward the end wall 332 to draw or pump diesel fuel from the diesel fuel line 38 into the pumping device 272, when the voltage is removed from the electrical coil 310. The electrical coil 310 is disposed around the bobbin 312 in the region 344 of the interior space 340.

Before proceeding with a detailed explanation of determining a cloud point temperature utilizing the pumping device 272, a brief explanation of pressure levels in the pumping device 272 will be explained. When the diesel fuel within the pumping device 272 is cooled by thermal device 274 such that it is at or below the cloud point temperature, the viscosity level of the diesel fuel is relatively high due to wax crystals forming in the diesel fuel. Further, when the controller 280 induces the armature 306 to move in a second direction (rightwardly from the position in FIG. 6), the wax crystals inhibit flow of the diesel fuel in chamber 346 through the restriction member 302 which increases the pressure within the chamber 346. When the pressure within the chamber 346 is greater than or equal to a threshold pressure level, the controller 280 determines that the viscosity level of the diesel fuel is relatively high due to wax crystals formed therein. Further, when a relatively high viscosity level due to wax crystals is detected as the diesel fuel is cooled, the controller 280 can determine the cloud point temperature based on the signal from the temperature sensor 276. Thus, the pressure sensor may be termed a viscosity sensor and the pressure signal obtained therefrom may be termed a viscosity signal. In an alternative embodiment, the formation of wax crystals in the diesel fuel could be sensed utilizing a different methodology. For example, when the electrical coil 310 is de-energized and the viscosity level of the diesel fuel is relatively high due to wax crystals being present in the diesel fuel, the pressure in the chamber 346 will decrease below a predetermined pressure level. Accordingly, when the pressure in the chamber 346 is below the predetermined pressure level, the controller 280 can determine the cloud point temperature based on the signal from the temperature sensor 276. It should be noted that the amplitude or frequency of the pressure signal is a characteristic that is indicative of the viscosity level of the diesel fuel.

Figure 7:
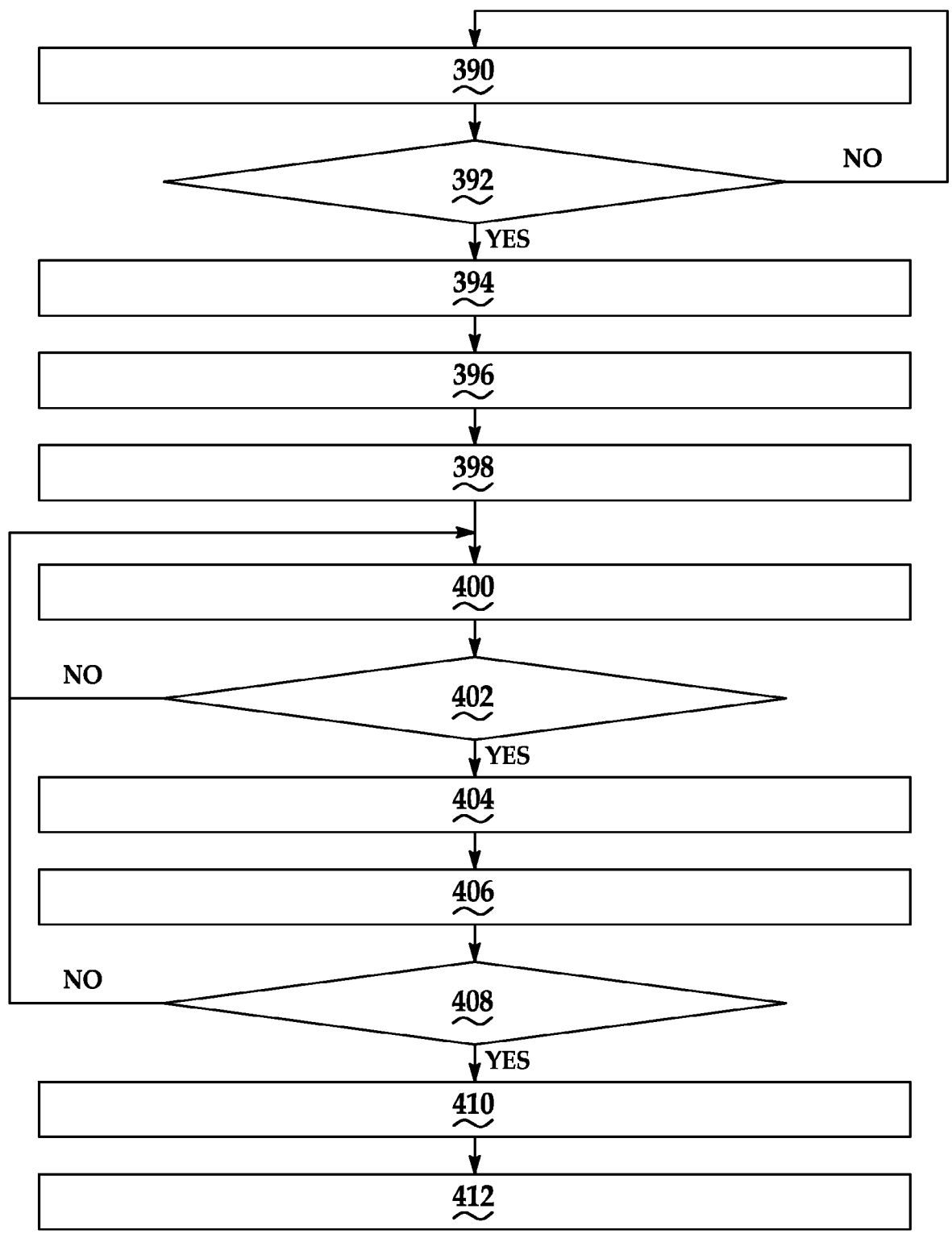
FIG. 7 is a flowchart of a method for determining a cloud point temperature value for diesel fuel utilizing the cloud point monitoring system of FIG. 6, in accordance with another exemplary embodiment.

Referring to FIG. 7, a flowchart of a method for determining a cloud point temperature value indicating a cloud point temperature of diesel fuel, utilizing the cloud point monitoring system 270, will now be explained with reference to steps 390-412. At step 390, the controller 280 receives a first temperature signal from the temperature sensor 276 indicative of a temperature of diesel fuel in the pumping device 272, and determines a first temperature value based on this signal. At step 392, the controller 280 makes a determination as to whether the first temperature value is within a first predetermined temperature range. If the value of step 392 equals "yes", the method advances to step 394. Otherwise, the method returns to step 390. At step 394, the controller 280 iteratively generates a first voltage to cycle the pumping device 272 to draw or pump fresh diesel fuel into the pumping device 272. At step 396, the controller 280 receives a second temperature signal from the temperature sensor 276 indicative of a temperature of diesel fuel in the pumping device 272, and determines a second temperature value based on this signal. At step 398, the controller 280 generates a cooling control signal to induce the thermal device 274 to cool diesel fuel in the pumping device 272. At step 400, the controller 280 receives a third temperature signal from the temperature sensor 276 indicative of a temperature of diesel fuel in the pumping device 272, and determines a third temperature value based on this signal. At step 402, the controller 280 makes a determination as to whether the third temperature value is less than or equal to a previous temperature value minus 2° C., or other decrement value suitable to indicate the temperature is changing. If the value of step 402 equals "yes", the method advances to step 404. Otherwise, the method returns to step 400. At step 404, the controller 280 generates a second voltage to induce the pumping device 272 to pump diesel fuel from the pumping device 272. At step 406, the controller 280 receives a pressure signal from the pressure sensor 278 fluidly communicating with diesel fuel in the pumping device 272 and determines a first pressure value based on the pressure signal, during generation of the second voltage. At step 408, the controller 280 makes a determination as to whether the diesel fuel is at a cloud point temperature, based on whether the pressure value is greater than a threshold pressure value. If the value of step 408 equals "yes", the method advances to step 410. Otherwise, the method returns to step 400. At step 410, the controller 280 sets a cloud point temperature value equal to the third temperature value and (i) displays the cloud point temperature value on the display device 284, and (ii) stores the cloud point temperature value in the memory device 282. At step 412, the controller 280 stops generating the cooling control signal to induce the thermal device 274 to stop cooling the diesel fuel in the pumping device 272. The method and steps 390-412 may be repeated continuously in conjunction with the operation of vehicle 10 or engine 20.

Figure 8:
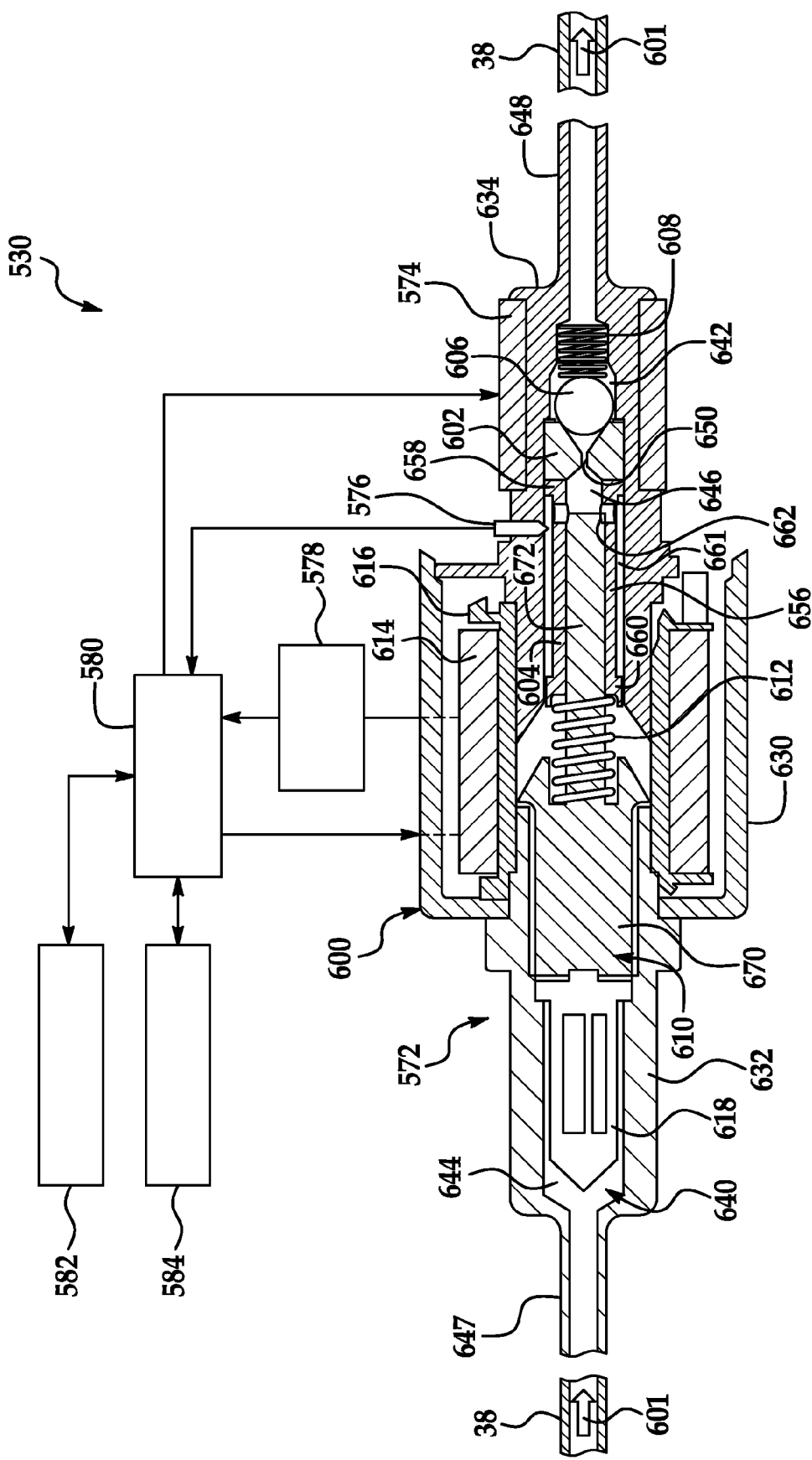
FIG. 8 is a schematic of yet another cloud point monitoring system utilized in the motor vehicle of FIG. 1, in accordance with a third exemplary embodiment.

Referring to FIG. 8, a third exemplary embodiment of a cloud point monitoring system 530 that can be utilized in the vehicle 10 will now be explained. The cloud point monitoring system 530 includes a pumping device 572, a thermal device 574, a temperature sensor 576, a current sensor 578, a controller 580, a memory device 582, and a display device 584. The cloud point monitoring system 530 is fluidly coupled to the diesel fuel conduit 38 and receives the diesel fuel flowing through the diesel fuel conduit 38, to determine the cloud point temperature of the diesel fuel. The operation of the cloud point monitoring system 530 is substantially similar to operation of the cloud point monitoring system 30, except that the pumping device 572 is a single-stroke flow-through pumping device.

The pumping device 572 is provided to pump diesel fuel from a first portion of the diesel fuel conduit 38 though the pumping device 572 and through another portion of the diesel fuel conduit 38 to the fuel filter 24, in response to control signals from the controller 580. The pumping device 572 includes a housing 600, a restriction member 602, a sleeve member 604, a check member 606, a spring 608, an armature 610, a spring 612, an electrical coil 614, a bobbin 616 and a filter 618.

The housing 600 is provided to enclose the remaining portions of the pumping device 572. The housing 600 includes a central wall 630, an inlet wall 632, and an outlet wall 634. The central wall 630 is substantially tubular-shaped. The inlet wall 632 is substantially tubular-shaped and is coupled to a first end of the central wall 630. The inlet wall 632 includes an inlet portion 647 further coupled to a first portion of the diesel fuel conduit 38 and fluidly communicates with the first portion of the diesel fuel conduit 38. The outlet wall 634 is substantially tubular-shaped and is coupled to a second end of the central wall 630. The outlet wall 634 includes an outlet portion 648 that is further coupled to a second portion of the diesel fuel conduit 38 and fluidly communicates with the second portion of the diesel fuel conduit 38. The central wall 630, the inlet wall 632, and the outlet wall 634 define an interior space 640.

The restriction member 602 is disposed in the interior space 640 proximate to the outlet wall 634. The restriction member 602 has an aperture 650 extending therethrough. The restriction member 602 partitions the interior space 640 into a region 642 and a region 644, including the space within chamber 646. The region 642 is disposed proximate to the second portion of the diesel fuel conduit 38 communicating with the fuel filter 24.

The sleeve member 604 is disposed in the region 644 proximate to the restriction member 602. The sleeve member 604 includes a tubular portion 656 and finger portions 658, 660. The finger portion 658 is disposed at a first end of the tubular portion 656 and contacts both the outlet wall 634 and the restriction member 602. The finger portion 660 is disposed at a second end of the tubular portion 656 within the outlet wall 634. Finger portion is disposed within inlet-outlet portion so as to permit fuel to flow between region 642 and region 644, including the space within the chamber 646. The tubular portion 656 includes an aperture 662 extending therethrough for allowing diesel fuel to flow therethrough into a gap 661 between the tubular portion 656 and the outlet wall 634.

The check member 606 and the spring 608 are disposed in the region 642 within the interior space 640. The check member 606 is disposed between the restriction member 602 and the spring 608. The spring 608 biases the check member 606 against the restriction member 602. Thus, the spring 608 and the check member 606 operate cooperatively as a check valve to prevent diesel fuel from flowing through the aperture 650 of the restriction member 602, unless a pressure of diesel fuel against the check member 606 exerts sufficient force to move the check member 606 away from the aperture 650 to allow diesel fuel to flow therethrough in the direction shown by arrow 601.

The armature 610 is provided to pump diesel fuel through the pumping device 572 when the armature 610 moves in the second direction (rightwardly from the position shown in FIG. 8) and to draw diesel fuel into the pumping device 572 when the armature 610 moves in a first direction (leftwardly to the position shown in FIG. 8) opposite the first direction. The armature 610 includes a body portion 670 coupled to a piston 672 and may be constructed from steel or other suitable materials. The armature 610 is disposed in the region 644 and the piston 672 is disposed within the tubular portion 656 of the sleeve member 604. The piston 672 is configured to slide within the sleeve member 606. The spring 612 is disposed around a portion of the piston 672, and a first end of the spring 612 abuts against the body portion 670 and a second end of the spring 612 abuts against the sleeve member 604. The spring 612 biases the armature 610 in the first direction (leftwardly to the position shown in FIG. 8). During operation, when the controller 580 applies a voltage on the electrical coil 614, the armature 610 moves in the second direction (rightwardly from the position shown in FIG. 8). Thereafter, when the controller 580 does not apply a voltage on the electrical coil 514, the spring 612 biases the armature 610 in the first direction (leftwardly to the position shown in FIG. 8).

The piston portion 672, the sleeve member 604, and the restriction member 602 define a chamber 646 in which diesel fuel is pumped through the aperture of the restriction member and past the check member 606 into the second portion of the diesel fuel conduit 38 fluidly communicating with the fuel filter 24.

The bobbin 616 is provided to support the electrical coil 614 thereon. The bobbin 616 is substantially tubular-shaped and is disposed on a portion of the inlet wall 632 extending in the interior space 640, and on a portion of the outlet wall 634 extending in the interior space 640. The bobbin 616 is constructed of a non-magnetic material.

The electrical coil 614 comprising a plurality of windings of a suitable conductive material is provided to receive a voltage from the controller 580 and to urge the armature 610 in a second direction (rightwardly from the position shown in FIG. 8) toward the restriction member 602 to pump diesel fuel from the pumping device 572 and chamber 646 into the second portion of the diesel fuel line 38 fluidly communicating with the fuel filter 24. The electrical coil 614 is further provided to allow the spring 612 to urge the armature 610 in a first direction (leftwardly to the position shown in FIG. 8) toward the filter 618 to draw diesel fuel from the first portion of the diesel fuel line 38 fluidly communicating with the feed pump 28 into the pumping device 572 and chamber 646, when the voltage is removed from the electrical coil 614. The electrical coil 614 is disposed around the bobbin 616 in the region 644 of the interior space 640.

The filter 618 is provided to filter diesel fuel that is pumped through the pumping device 572. The filter 618 is disposed in the region 644 of the interior space 640 proximate to the inlet wall 632. The filter 618 is further disposed between the armature 610 and the inlet portion 647.

The thermal device 574 is disposed adjacent to the outlet wall 634. The thermal device 574 is configured to cool the outlet wall 634 and the diesel fuel therein, and particularly the fuel in chamber 646, in response to receiving a control signal from the controller 580. In one exemplary embodiment, the thermal device 574 is a Peltier cell.

The temperature sensor 576 is disposed on the outlet wall 634 and fluidly communicates with the diesel fuel within the region 644. The temperature sensor 576 is configured to generate a signal indicative of a temperature of the diesel fuel in the region 644, and particularly the fuel within chamber 646 which is received by the controller 580.

The current sensor 578 is provided to generate a signal indicative of an amplitude of an electrical current in the electrical coil 614, which is received by the controller 580. The current sensor 578 is electrically coupled to the electrical coil 614 and to the controller 580.

The controller 580 is electrically coupled to the thermal device 574, the temperature sensor 576, the current sensor 578, the memory device 582, the display device 584, and the electrical coil 614. The controller 580 is provided to determine a cloud point temperature of the diesel fuel based on signals received from the temperature sensor 576 and the current sensor 578, in a substantially similar manner as described above for controller 78 of system 30. In one exemplary embodiment, the controller 580 comprises a microprocessor. The memory device 582 is provided to store data and values generated by the controller 580 therein. The display device 584 is provided to display data and values generated by the controller 580.

Figure 9:
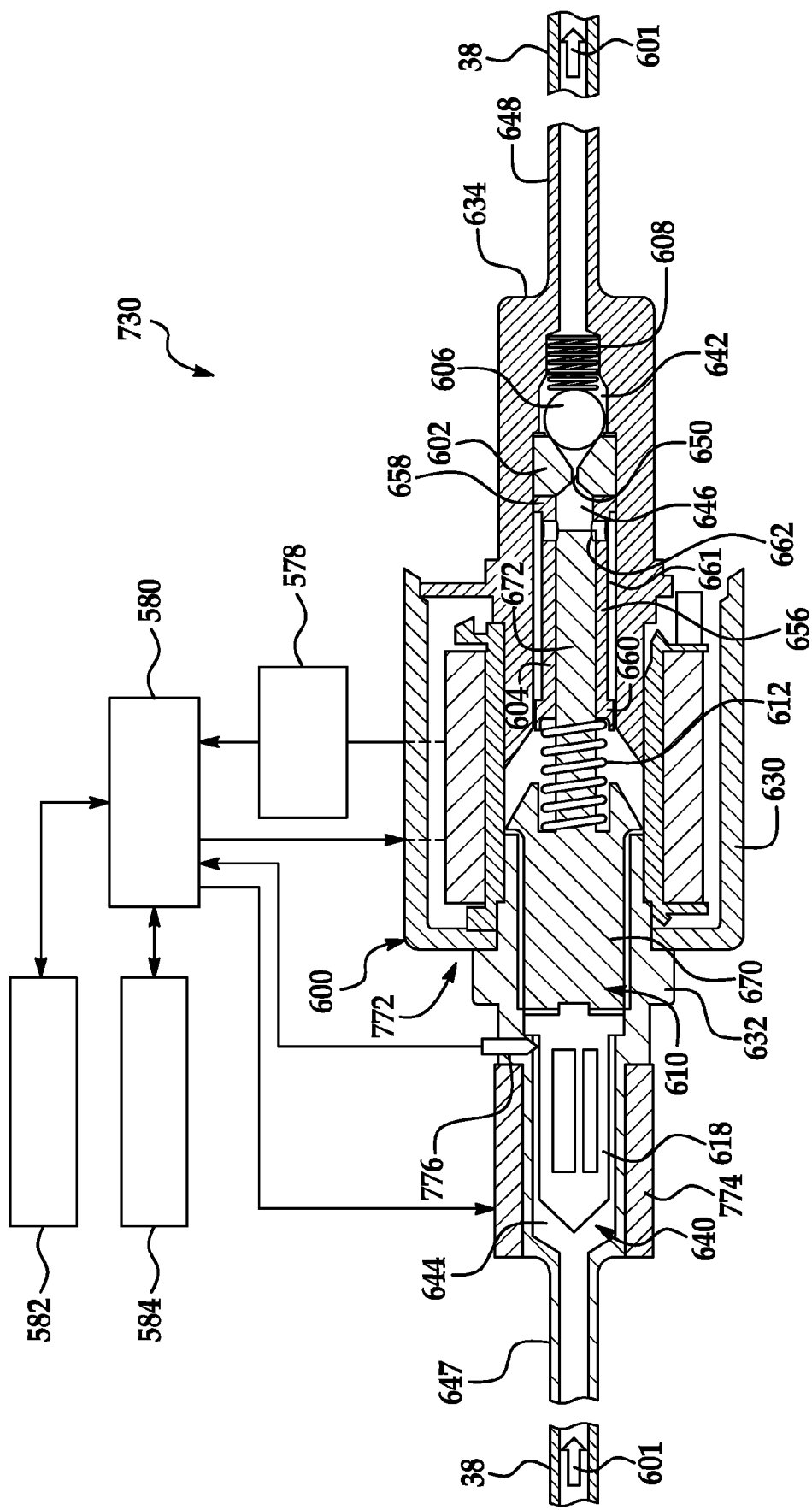
FIG. 9 is a schematic of yet another cloud point monitoring system that can be utilized in the motor vehicle of FIG. 1, in accordance with a fourth exemplary embodiment.

Referring to FIG. 9, a fourth exemplary embodiment of a cloud point monitoring system 730 that can be utilized in the vehicle 10 will now be explained. The cloud point monitoring system 730 includes the pumping device 772, a thermal device 774, a temperature sensor 776, the current sensor 578, the controller 580, the memory device 582, and the display device 584. The cloud point monitoring system 730 is fluidly coupled to the diesel fuel conduit 38 and receives the diesel fuel flowing through the diesel fuel conduit 38, to determine the cloud point temperature of the diesel fuel. The primary difference between the cloud point monitoring system 730 and the cloud point monitoring system 530 are the locations of the temperature sensor 776 and the thermal device 774. In the cloud point monitoring system 730, the temperature sensor 776 is disposed on the inlet wall 632 and fluidly communicates with the diesel fuel in the interior space of the pumping device 772. Further, the thermal device 774 is disposed on the inlet wall 632 and is configured to cool the inlet wall 632 and diesel fuel within the interior space 640 of the pumping device 772. Thus, diesel fuel is cooled as it enters pumping device 774 and region 644 and passes into chamber 646. However, the cooled diesel fuel in region 644 and chamber 646 produces a similar current response during operation of system 730 as described above with regard to cloud point monitoring systems 30 and 530.

Figure 10:
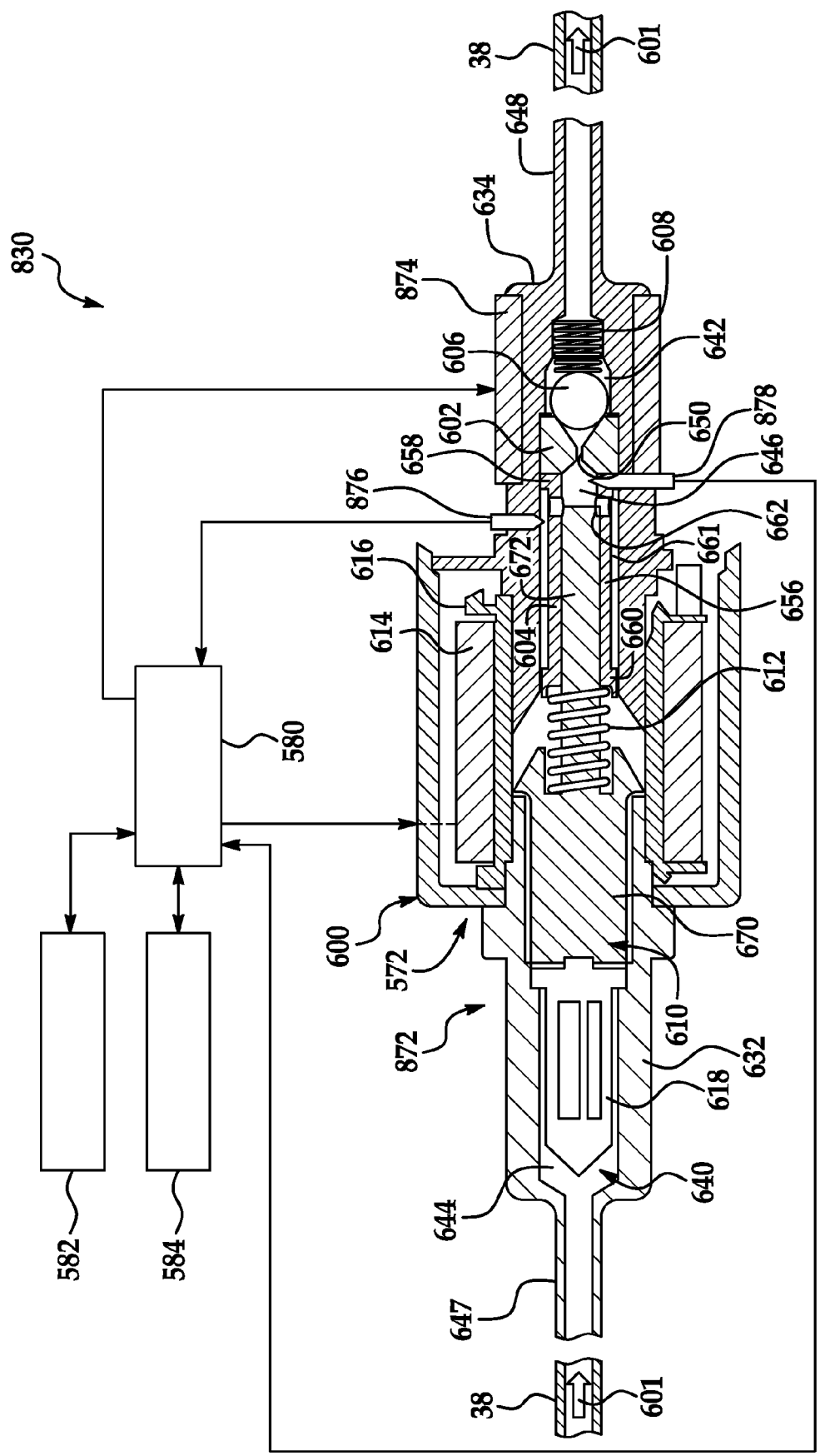
FIG. 10 is a schematic of yet another cloud point monitoring system that can be utilized in the motor vehicle of FIG. 1, in accordance with a fifth exemplary embodiment.

Referring to FIG. 10, a fifth exemplary embodiment of a cloud point monitoring system 830 that can be utilized in the vehicle 10 will now be explained. The cloud point monitoring system 830 includes a pumping device 872, a thermal device 874, a temperature sensor 876, a pressure sensor 878, a controller 580, a memory device 582, and a display device 584. The cloud point monitoring system 830 is fluidly coupled to the diesel fuel conduit 38 and receives the diesel fuel flowing through the diesel fuel conduit 38, to determine the cloud point temperature of the diesel fuel.

The pumping device 872 is provided to pump diesel fuel from a first portion of the diesel fuel conduit 38 into the pumping device 872 and to pump the diesel fuel from the pumping device 872 into a second portion of the diesel fuel conduit 38, in response to a control signals from the controller 580. The pumping device 872 includes a housing 600, a restriction member 602, a sleeve member 604, a check member 606, a spring 608, an armature 610, a spring 612, an electrical coil 614, a bobbin 616, and a filter 618. The pumping device 872 operates in a substantially similar manner as the pumping device 572 described above.

The housing 600 is provided to enclose the remaining portions of the pumping device 872. The housing 600 includes a central wall 630, an inlet wall 632, and an outlet wall 634.

The controller 580 is electrically coupled to the thermal device 874, the temperature sensor 876, the pressure sensor 878, the memory device 582, the display device 584, and the electrical coil 614. The controller 580 is provided to determine a cloud point temperature of the diesel fuel based on signals received from the temperature sensor 576 and the pressure sensor 878, in a substantially similar manner as the controller 280 of the system 270. Further, the controller 580 is configured to control the pumping device 872 in a substantially similar manner as the controller 580 controls the pumping device 572 (see FIG. 8). In one exemplary embodiment, the controller 580 comprises a microprocessor. The memory device 582 is provided to store data and values generated by the controller 580 therein. The display device 584 is provided to display data and values generated by the controller 580.

Figure 11:
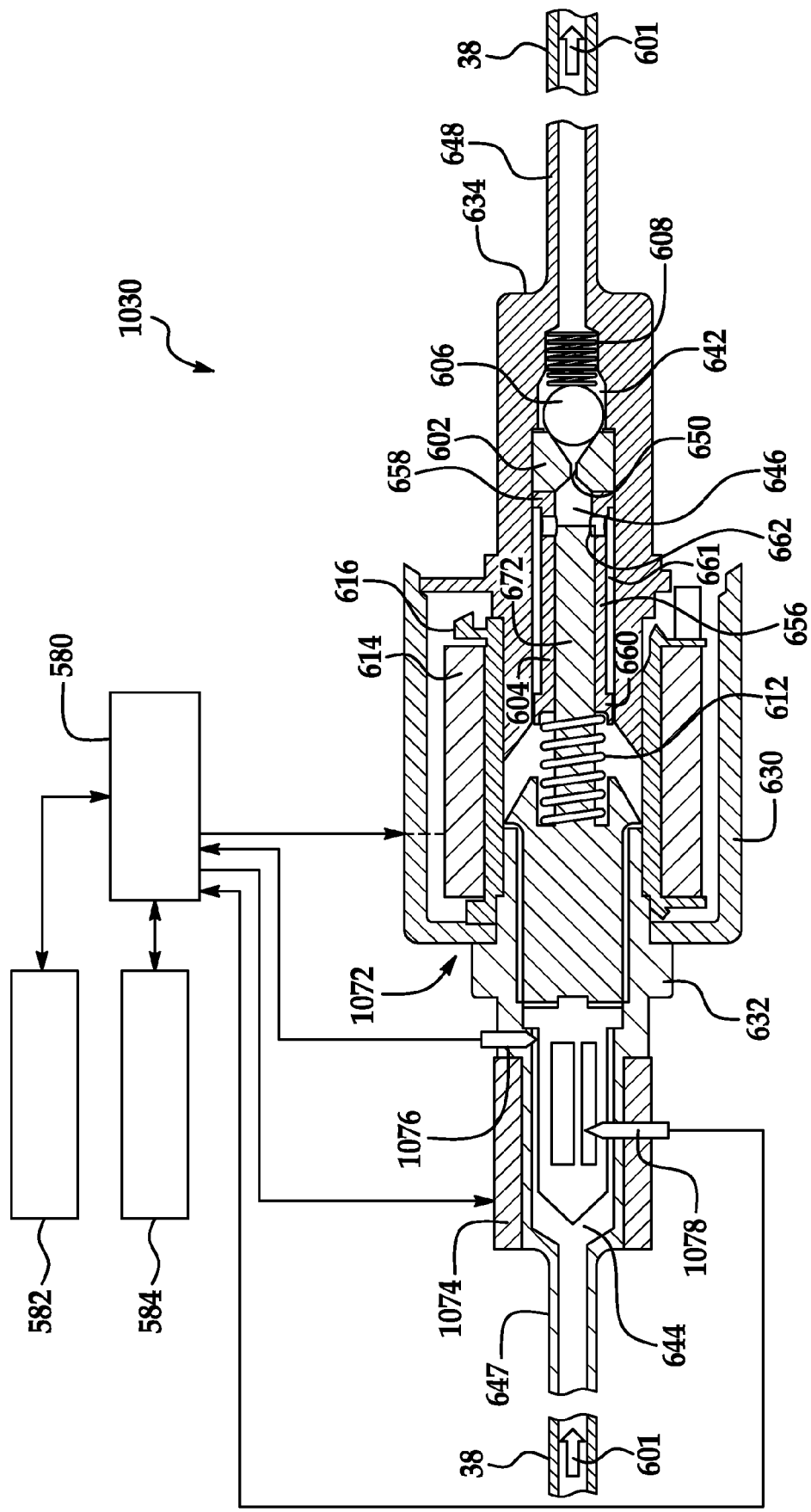
FIG. 11 is a schematic of yet another cloud point monitoring system that can be utilized in the motor vehicle of FIG. 1, in accordance with a sixth exemplary embodiment.

Referring to FIG. 11, a sixth embodiment of cloud point monitoring system 1030 that can be utilized in the vehicle 10 will now be explained. The cloud point monitoring system 1030 includes the pumping device 1072, a thermal device 1074, a temperature sensor 1076, a pressure sensor 1078, the controller 580, the memory device 582, and the display device 584. The cloud point monitoring system 1030 is fluidly coupled to the diesel fuel conduit 38 and receives the diesel fuel flowing through the diesel fuel conduit 38, to determine the cloud point temperature of the diesel fuel. The primary difference between the cloud point monitoring system 1030 and the cloud point monitoring system 830 are the locations of the temperature sensor 1076, the pressure sensor 1078, and the thermal device 1074. In the cloud point monitoring system 1030, the temperature sensor 1076 and the pressure sensor 1078 are disposed on the inlet wall 632 and fluidly communicate with the diesel fuel in the interior space of the pumping device 1072. Further, the thermal device 1074 is disposed on the inlet wall 632 and is configured to cool the inlet wall 632 and diesel fuel within the interior space of the pumping device 1072. Further, during operation, when the electrical coil 614 is energized and wax crystals have formed in the diesel fuel, the pressure level detected by the pressure sensor 1078 will be less than a threshold pressure value. Accordingly, at that time, the controller 580 can determine the cloud point temperature based on the signal from the temperature sensor 1076.

These cloud point monitoring systems for determining a cloud point temperature value for diesel fuel represent a substantial advantage over other systems and methods. In particular, the exemplary embodiments of a cloud point monitoring system provide a technical effect of determining a viscosity level of diesel fuel and a temperature of the diesel fuel to determine a cloud point temperature value indicating a cloud point temperature of the diesel fuel.

While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiments disclosed as the best mode contemplated for carrying out this invention, but that the invention will include all embodiments falling within the scope of the present application.

What is claimed is:

1. A cloud point monitoring system, comprising:
a pumping device configured to pump diesel fuel therefrom in response to a voltage being applied to the pumping device;
a temperature sensor configured to generate a temperature signal indicating a temperature of diesel fuel in the pumping device;
a viscosity sensor configured to generate a viscosity signal having a characteristic indicative of a viscosity level of the diesel fuel in the pumping device; and
a controller configured to generate the voltage to induce the pumping device to pump diesel fuel therefrom, the controller further configured to determine a temperature value based on the temperature signal, the controller further configured to determine a cloud point temperature value associated with the diesel fuel based on the temperature value and the characteristic of the viscosity signal, wherein the viscosity sensor comprises a current sensor configured to generate a current signal indicative of an electrical current in the pumping device, and wherein the controller is further configured to monitor the current signal to determine a time interval associated with the electrical current that the pumping device utilizes to pump diesel fuel therefrom, the time interval being the characteristic indicative of the viscosity level of the diesel fuel, the controller configured to set the cloud point temperature value equal to the temperature value when the time interval is greater than or equal to a threshold time interval value.

2. The cloud point monitoring system of claim 1, further comprising a thermal device operably coupled to the pumping device, the thermal device configured to cool the diesel fuel in the pumping device in response to a cooling control signal.

3. The cloud point monitoring system of claim 2, wherein the controller is further configured to generate the cooling control signal to induce the thermal device to cool diesel fuel in the pumping device.

4. The cloud point monitoring system of claim 1, wherein the pumping device is one of a single-stroke flow-through pumping device and a single-stroke pumping device.

5. A cloud point monitoring system, comprising:
a pumping device configured to pump diesel fuel therefrom in response to a voltage being applied to the pumping device;
a temperature sensor configured to generate a temperature signal indicating a temperature of diesel fuel in the pumping device;
a viscosity sensor configured to generate a viscosity signal having a characteristic indicative of a viscosity level of the diesel fuel in the pumping device; and
a controller configured to generate the voltage to induce the pumping device to pump diesel fuel therefrom the controller further configured to determine a temperature value based on the temperature signal, the controller further configured to determine a cloud point temperature value associated with the diesel fuel based on the temperature value and the characteristic of the viscosity signal, wherein the viscosity sensor is comprises a pressure sensor configured to generate the viscosity signal having a frequency or amplitude indicating a pressure of diesel fuel in the pumping device which is indicative of the viscosity level of the diesel fuel in the pumping device, the frequency or amplitude of the viscosity signal being the characteristic indicative of the viscosity level of the diesel fuel in the pumping device, and wherein the controller is further configured to determine a pressure value based on the viscosity signal, the controller further configured to determine the cloud point temperature value associated with the diesel fuel based on the temperature value and the pressure value.

6. The cloud point monitoring system of claim 5, wherein the controller is configured to set the cloud point temperature value equal to the temperature value when the pressure value is greater than or equal to or less than or equal to a threshold pressure value.

7. A cloud point monitoring system, comprising:
a pumping device configured to pump diesel fuel therefrom in response to a voltage being applied to the pumping device, the pumping device having a housing, a restriction member, an armature, and an electrical coil, the housing having an outer wall defining an interior space and an inlet-outlet portion, the restriction member separating the interior space into first and second regions, the second region fluidly communicating with the inlet-outlet portion, the restriction member having an aperture extending therethrough, the armature being disposed in the first region of the interior space, the armature having a piston, such that a chamber is formed in the first region between the piston and the restriction member, the electrical coil being disposed proximate the first region of the interior space, around the armature, such that when the voltage is applied to the electrical coil, the piston is operative to move toward the restriction member to pump diesel fuel disposed in the chamber through the aperture to both the second region and the inlet-output portion, and when the voltage is subsequently not applied to the electrical coil, the piston is operative to move away from the restriction member to pump diesel fuel disposed in the second region through the aperture into the chamber;
a temperature sensor configured to generate a temperature signal indicating a temperature of diesel fuel in the pumping device;
a viscosity sensor configured to generate a viscosity signal having a characteristic indicative of a viscosity level of the diesel fuel in the pumping device; and
a controller configured to generate the voltage to induce the pumping device to pump diesel fuel therefrom the controller further configured to determine a temperature value based on the temperature signal, the controller further configured to determine a cloud point temperature value associated with the diesel fuel based on the temperature value and the characteristic of the viscosity signal.

8. The cloud point monitoring system of claim 7, wherein the temperature sensor is disposed proximate to the chamber.

9. A cloud point monitoring system, comprising
a pumping device configured to pump diesel fuel therefrom in response to a voltage being applied to the pumping device, the pumping device having a housing, a restriction member, an armature, and an electrical coil; the housing having an outer wall defining an interior space, an inlet portion, and an outlet portion spaced from the inlet portion, the restriction member separating the interior space into first and second regions, the first region fluidly communicating with the first inlet portion, the second region fluidly communicating with the outlet portion, the restriction member having an aperture extending therethrough, the armature being disposed in the first region of the interior space, the armature having a piston, such that a chamber is formed in the first region between the piston and the restriction member, the electrical coil being disposed proximate the first region of the interior space, the electrical coil being disposed around the armature, such that when the voltage is applied to the electrical coil, the piston is operative to move toward the restriction member to pump diesel fuel disposed in the chamber through the aperture into the second region and the outlet portion, and when the voltage is subsequently not applied to the electrical coil, the piston is operative to move away from the restriction member to pump diesel fuel from the inlet portion into the chamber;
a temperature sensor configured to generate a temperature signal indicating a temperature of diesel fuel in the pumping device;
a viscosity sensor configured to generate a viscosity signal having a characteristic indicative of a viscosity level of the diesel fuel in the pumping device; and
a controller configured to generate the voltage to induce the pumping device to pump diesel fuel therefrom the controller further configured to determine a temperature value based on the temperature signal, the controller further configured to determine a cloud point temperature value associated with the diesel fuel based on the temperature value and the characteristic of the viscosity signal.

10. The cloud point monitoring system of claim 9, wherein the temperature sensor is disposed proximate to the chamber.

11. The cloud point monitoring system of claim 9, wherein the temperature sensor is disposed proximate to the first region of the interior space.

12. A motor vehicle, comprising:
a diesel engine configured to receive diesel fuel from a fuel tank; and
a cloud point monitoring system receiving a portion of the diesel fuel from the fuel tank, the cloud point monitoring system having:
a pumping device configured to receive the portion of the diesel fuel and to pump diesel fuel therefrom in response to a voltage being applied to the pumping device;
a temperature sensor configured to generate a temperature signal indicating a temperature of diesel fuel in the pumping device;
a viscosity sensor configured to generate a viscosity signal having a characteristic indicative of a viscosity level of the diesel fuel in the pumping device; and
a controller configured to generate the voltage to induce the pumping device to pump the diesel fuel therefrom, the controller further configured to determine a temperature value based on the temperature signal, the controller further configured to determine a cloud point temperature value associated with the diesel fuel based on the temperature value and the characteristic of the viscosity signal, wherein the viscosity sensor comprises a current sensor configured to generate the viscosity signal indicative of an electrical current in the pumping device, and wherein the controller is further configured to monitor the viscosity signal to determine a time interval associated with the electrical current that the pumping device utilizes to pump diesel fuel therefrom, the time interval being the characteristic indicative of the viscosity level of the diesel fuel, the controller configured to set the cloud point temperature value equal to the temperature value when the time interval is greater than or equal to a threshold time interval value.

13. The motor vehicle of claim 12, wherein the cloud point monitoring system further has a thermal device operably coupled to the pumping device, the thermal device configured to cool the diesel fuel in the pumping device in response to a cooling control signal.

14. A motor vehicle, comprising:
a diesel engine configured to receive diesel fuel from a fuel tank; and
a cloud point monitoring system receiving a portion of the diesel fuel from the fuel tank, the cloud point monitoring system having:
a pumping device configured to receive the portion of the diesel fuel and to pump diesel fuel therefrom in response to a voltage being applied to the pumping device;
a temperature sensor configured to generate a temperature signal indicating a temperature of diesel fuel in the pumping device;
a viscosity sensor configured to generate a viscosity signal having a characteristic indicative of a viscosity level of the diesel fuel in the pumping device; and
a controller configured to generate the voltage to induce the pumping device to pump the diesel fuel therefrom, the controller further configured to determine a temperature value based on the temperature signal, the controller further configured to determine a cloud point temperature value associated with the diesel fuel based on the temperature value and the characteristic of the viscosity signal, wherein the viscosity sensor comprises a pressure sensor configured to generate the pressure signal having an amplitude or frequency indicating a pressure of diesel fuel in the pumping device, the amplitude or frequency being the characteristic indicative of the viscosity level of the diesel fuel in the pumping device, and wherein the controller is further configured to determine a pressure value based on the viscosity signal, the controller further configured to determine the cloud point temperature value associated with the diesel fuel based on the temperature value and the pressure value.

15. The motor vehicle of claim 14, wherein the cloud point monitoring system further has a thermal device operably coupled to the pumping device, the thermal device configured to cool the diesel fuel in the pumping device in response to a cooling control signal.

* * * * *